(12) United States Patent
Surti et al.

(10) Patent No.: US 8,864,781 B2
(45) Date of Patent: Oct. 21, 2014

(54) INTESTINAL BYPASS USING MAGNETS

(75) Inventors: Vihar C. Surti, Winston-Salem, NC (US); Travis E. Dillon, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1764 days.

(21) Appl. No.: 12/025,985

(22) Filed: Feb. 5, 2008

(65) Prior Publication Data

US 2008/0208224 A1    Aug. 28, 2008

Related U.S. Application Data (60) Provisional application No. 60/904,084, filed on Feb. 28, 2007.

(51) Int. Cl.
| | | |
|---|---|---|
| *A61B 17/08* | (2006.01) | |
| *A61B 17/00* | (2006.01) | |
| *A61B 17/11* | (2006.01) | |

(52) U.S. Cl.
CPC ....... *A61B 17/1114* (2013.01); *A61B 2017/003* (2013.01); *A61B 2017/1103* (2013.01); *A61B 2017/1139* (2013.01); *A61B 2017/00876* (2013.01)
USPC ........................................................ 606/153

(58) Field of Classification Search
USPC .................................................. 606/151, 153
See application file for complete search history.

(56) References Cited

U.S. PATENT DOCUMENTS

| | | | |
|---|---|---|---|
| 3,299,883 A | | 1/1967 | Rubens |
| 3,358,676 A | | 12/1967 | Frei et al. |
| 3,674,014 A | | 7/1972 | Tillander |
| 3,709,214 A | | 1/1973 | Robertson |
| 4,022,208 A | | 5/1977 | Valtchev |
| 4,899,744 A | | 2/1990 | Fujitsuka et al. |
| 5,081,997 A | | 1/1992 | Bosley et al. |
| 5,297,536 A | | 3/1994 | Wilk |
| 5,346,501 A | | 9/1994 | Regula et al. |
| 5,411,508 A | * | 5/1995 | Bessler et al. ................ 606/153 |
| 5,429,131 A | | 7/1995 | Scheinman et al. |
| 5,441,507 A | * | 8/1995 | Wilk ............................ 606/139 |
| 5,458,131 A | | 10/1995 | Wilk |
| 5,624,430 A | * | 4/1997 | Eton et al. ........................ 606/1 |
| 5,690,656 A | | 11/1997 | Cope et al. |
| 6,015,414 A | | 1/2000 | Werp et al. |

(Continued)

FOREIGN PATENT DOCUMENTS

| | | |
|---|---|---|
| EP | 1077047 A2 | 2/2001 |
| EP | 1493391 A1 | 1/2005 |

OTHER PUBLICATIONS

Hagen, et al., Hybrid natural orifice transluminal endoscopic surgery (NOTES) for Roux-en-Y gastric bypass: an experimental surgical study in human cadavers, 2008, pp. 918-924, vol. 40.

(Continued)

*Primary Examiner* — Corrine M McDermott
*Assistant Examiner* — Alexander Orkin
(74) *Attorney, Agent, or Firm* — Brinks Gilson & Lione (57) ABSTRACT

Medical devices and methods are provided for forming an intestinal bypass anastomosis, such as for treatment of obesity. The medical devices and methods are minimally invasive and reduce complications. Two magnet assemblies are deployed in a spaced apart relationship, and are transluminally brought together to approximate the tissue and form an anastomosis therebetween.

19 Claims, 9 Drawing Sheets

(56) References Cited

U.S. PATENT DOCUMENTS

| | | | |
|---|---|---|---|
| 6,030,365 A | 2/2000 | Laufer | |
| 6,156,006 A | 12/2000 | Brosens et al. | |
| 6,293,952 B1 | 9/2001 | Brosens et al. | |
| 6,464,665 B1* | 10/2002 | Heuser | 604/104 |
| 6,527,753 B2 | 3/2003 | Sekine et al. | |
| 6,535,764 B2 | 3/2003 | Imran et al. | |
| 6,572,629 B2 | 6/2003 | Kalloo et al. | |
| 6,655,386 B1* | 12/2003 | Makower et al. | 128/898 |
| 6,689,062 B1 | 2/2004 | Mesallum | |
| 6,802,847 B1* | 10/2004 | Carson et al. | 606/153 |
| 6,918,871 B2 | 7/2005 | Schulze | |
| 7,128,708 B2 | 10/2006 | Saadat et al. | |
| 7,232,448 B2 | 6/2007 | Battles et al. | |
| 7,273,451 B2 | 9/2007 | Sekine et al. | |
| 7,351,202 B2 | 4/2008 | Long | |
| 7,431,694 B2 | 10/2008 | Stefanchik et al. | |
| 7,585,308 B2 | 9/2009 | Weisenburgh, II et al. | |
| 7,591,828 B2 | 9/2009 | Ortiz | |
| 7,608,086 B2 | 10/2009 | Tanaka et al. | |
| 7,618,427 B2 | 11/2009 | Ortiz et al. | |
| 7,637,919 B2* | 12/2009 | Ishikawa et al. | 606/153 |
| 7,654,951 B2 | 2/2010 | Ishikawa | |
| 7,666,197 B2 | 2/2010 | Orban, III | |
| 7,691,103 B2 | 4/2010 | Fernandez et al. | |
| 7,708,748 B2 | 5/2010 | Weisenburgh, II et al. | |
| 7,713,278 B2 | 5/2010 | Hess et al. | |
| 7,725,214 B2 | 5/2010 | Diolaiti | |
| 2001/0049497 A1 | 12/2001 | Kalloo et al. | |
| 2002/0022851 A1 | 2/2002 | Kalloo et al. | |
| 2003/0216613 A1 | 11/2003 | Suzuki et al. | |
| 2003/0225312 A1 | 12/2003 | Suzuki et al. | |
| 2004/0073238 A1* | 4/2004 | Makower | 606/153 |
| 2004/0087985 A1 | 5/2004 | Loshakove et al. | |
| 2004/0092975 A1 | 5/2004 | Loshakove et al. | |
| 2004/0097801 A1 | 5/2004 | Mesallum | |
| 2004/0225191 A1 | 11/2004 | Sekine et al. | |
| 2004/0249367 A1 | 12/2004 | Saadat et al. | |
| 2005/0004584 A1 | 1/2005 | Franco et al. | |
| 2005/0101837 A1 | 5/2005 | Kalloo et al. | |
| 2005/0107664 A1 | 5/2005 | Kalloo et al. | |
| 2006/0025654 A1 | 2/2006 | Suzuki et al. | |
| 2006/0025788 A1 | 2/2006 | Loshakove et al. | |
| 2006/0036267 A1 | 2/2006 | Saadat et al. | |
| 2006/0100480 A1 | 5/2006 | Ewers et al. | |
| 2006/0167482 A1 | 7/2006 | Swain et al. | |
| 2006/0178560 A1 | 8/2006 | Saadat et al. | |
| 2006/0200004 A1 | 9/2006 | Wilk | |
| 2006/0211919 A1 | 9/2006 | Wilk | |
| 2006/0212063 A1 | 9/2006 | Wilk | |
| 2006/0229653 A1 | 10/2006 | Wilk | |
| 2006/0237022 A1 | 10/2006 | Chen et al. | |
| 2006/0237023 A1 | 10/2006 | Cox et al. | |
| 2006/0241344 A1 | 10/2006 | Wilk | |
| 2006/0241480 A1 | 10/2006 | Wilk | |
| 2006/0241570 A1 | 10/2006 | Wilk | |
| 2006/0241651 A1 | 10/2006 | Wilk | |
| 2006/0252997 A1 | 11/2006 | Wilk | |
| 2006/0253123 A1 | 11/2006 | Wilk | |
| 2006/0258909 A1 | 11/2006 | Saadat et al. | |
| 2006/0287666 A1 | 12/2006 | Saadat et al. | |
| 2007/0004958 A1 | 1/2007 | Ohdaira | |
| 2007/0051380 A1 | 3/2007 | Pasricha | |
| 2007/0100375 A1 | 5/2007 | Mikkaichi et al. | |
| 2007/0100376 A1 | 5/2007 | Mikkaichi et al. | |
| 2007/0106313 A1 | 5/2007 | Golden et al. | |
| 2007/0112362 A1 | 5/2007 | Mikkaichi et al. | |
| 2007/0123840 A1 | 5/2007 | Cox | |
| 2007/0163585 A1 | 7/2007 | Uesugi et al. | |
| 2007/0163596 A1 | 7/2007 | Mikkaichi et al. | |
| 2007/0163604 A1 | 7/2007 | Mikkaichi et al. | |
| 2007/0167675 A1 | 7/2007 | Miyamoto et al. | |
| 2007/0167676 A1 | 7/2007 | Miyamoto et al. | |
| 2007/0167967 A1 | 7/2007 | Mikkaichi et al. | |
| 2007/0173859 A1 | 7/2007 | Mikkaichi et al. | |
| 2007/0197864 A1 | 8/2007 | Dejima et al. | |
| 2007/0198000 A1 | 8/2007 | Miyamoto et al. | |
| 2007/0198033 A1 | 8/2007 | Kalloo et al. | |
| 2007/0208360 A1 | 9/2007 | Demarais et al. | |
| 2007/0213702 A1 | 9/2007 | Kogosaka et al. | |
| 2007/0213749 A1 | 9/2007 | Kogosaka et al. | |
| 2007/0219411 A1 | 9/2007 | Dejima et al. | |
| 2007/0225734 A1 | 9/2007 | Bell et al. | |
| 2007/0255100 A1 | 11/2007 | Barlow et al. | |
| 2007/0255165 A1 | 11/2007 | Uesugi et al. | |
| 2007/0255273 A1 | 11/2007 | Fernandez et al. | |
| 2007/0260214 A1 | 11/2007 | Mikkaichi et al. | |
| 2007/0270629 A1 | 11/2007 | Charles | |
| 2007/0276378 A1* | 11/2007 | Harrison et al. | 606/61 |
| 2008/0015408 A1 | 1/2008 | Paolitto et al. | |
| 2008/0021277 A1 | 1/2008 | Stefanchik | |
| 2008/0064921 A1 | 3/2008 | Larkin et al. | |
| 2008/0064927 A1 | 3/2008 | Larkin et al. | |
| 2008/0064931 A1 | 3/2008 | Schena et al. | |
| 2008/0065097 A1 | 3/2008 | Duval et al. | |
| 2008/0065098 A1 | 3/2008 | Larkin | |
| 2008/0065099 A1 | 3/2008 | Cooper et al. | |
| 2008/0065100 A1 | 3/2008 | Larkin | |
| 2008/0065101 A1 | 3/2008 | Larkin | |
| 2008/0065102 A1 | 3/2008 | Cooper | |
| 2008/0065103 A1 | 3/2008 | Cooper et al. | |
| 2008/0065104 A1 | 3/2008 | Larkin et al. | |
| 2008/0065105 A1 | 3/2008 | Larkin et al. | |
| 2008/0065106 A1 | 3/2008 | Larkin | |
| 2008/0065107 A1 | 3/2008 | Larkin et al. | |
| 2008/0065108 A1 | 3/2008 | Diolaiti | |
| 2008/0065109 A1 | 3/2008 | Larkin | |
| 2008/0065110 A1 | 3/2008 | Duval et al. | |
| 2008/0071288 A1 | 3/2008 | Larkin et al. | |
| 2008/0071289 A1 | 3/2008 | Cooper et al. | |
| 2008/0071290 A1 | 3/2008 | Larkin et al. | |
| 2008/0071291 A1 | 3/2008 | Duval et al. | |
| 2008/0114378 A1 | 5/2008 | Matsushita | |
| 2008/0119868 A1 | 5/2008 | Sharp et al. | |
| 2008/0125804 A1 | 5/2008 | Gostout | |
| 2008/0154290 A1 | 6/2008 | Golden et al. | |
| 2008/0161641 A1 | 7/2008 | Nakazato et al. | |
| 2008/0171907 A1 | 7/2008 | Long et al. | |
| 2008/0183039 A1 | 7/2008 | Long et al. | |
| 2008/0200762 A1 | 8/2008 | Stokes et al. | |
| 2008/0208161 A1 | 8/2008 | Kaji et al. | |
| 2008/0228029 A1 | 9/2008 | Mikkaichi et al. | |
| 2008/0228203 A1 | 9/2008 | Bell et al. | |
| 2008/0249416 A1 | 10/2008 | Sato | |
| 2008/0275297 A1 | 11/2008 | Bakos et al. | |
| 2008/0287963 A1 | 11/2008 | Rogers et al. | |
| 2008/0312502 A1 | 12/2008 | Swain et al. | |
| 2009/0023985 A1 | 1/2009 | Ewers | |
| 2009/0054728 A1 | 2/2009 | Trusty | |
| 2009/0054761 A1 | 2/2009 | Voegele et al. | |
| 2009/0182195 A1 | 7/2009 | Faller et al. | |
| 2009/0221915 A1 | 9/2009 | Voegele et al. | |
| 2009/0227828 A1 | 9/2009 | Swain et al. | |
| 2009/0276055 A1 | 11/2009 | Harris et al. | |
| 2009/0281559 A1 | 11/2009 | Swain et al. | |
| 2010/0010520 A1 | 1/2010 | Takahashi et al. | |
| 2010/0036399 A1 | 2/2010 | Viola | |
| 2010/0056861 A1 | 3/2010 | Spivey | |
| 2010/0063521 A1 | 3/2010 | Manzo | |
| 2010/0087842 A1 | 4/2010 | Heinrich et al. | |
| 2010/0094319 A1 | 4/2010 | Heinrich et al. | |
| 2010/0099947 A1 | 4/2010 | Sato et al. | |
| 2010/0113872 A1 | 5/2010 | Asada et al. | |
| 2010/0114124 A1 | 5/2010 | Kelleher et al. | |
| 2010/0160729 A1 | 6/2010 | Smith et al. | |
| 2010/0179510 A1 | 7/2010 | Fox et al. | |
| 2010/0179540 A1 | 7/2010 | Marczyk et al. | |
| 2010/0198232 A1 | 8/2010 | Diolaiti | |

OTHER PUBLICATIONS

Fritscher-Ravens, EUS—Experimental and Evolving Techniques, 2006, pp. S95-S99, vol. 38.

Fritscher-Ravens, et al., Comparative study of NOTES alone vs. EUS-guided NOTES procedures, 2008, pp. 925-930, vol. 40.

(56) References Cited

OTHER PUBLICATIONS

Bories, et al., Transgastric endoscopic ultrasonography-guided biliary drainage: results of a pilot study, 2007, pp. 287-291, vol. 39.
Will, et al., Treatment of biliary obstruction in selected patients by endoscopic ultrasonography (EUS)-guided transluminal biliary drainage, 2007, pp. 292-295, vol. 39.

EPO Office Action dated Aug. 6, 2010 in related EP Application No. 08729010,2.
International Preliminary Report on Patentability in related PCT/US2008/053011 dated Sep. 1, 2009.
International Search Report & Written Opinion (Jul. 8, 2008).

\* cited by examiner

INTESTINAL BYPASS USING MAGNETS

CROSS-REFERENCE TO RELATED APPLICATIONS

This application claims the benefit of U.S. Provisional Application Ser. No. 60/904,084 filed on Feb. 28, 2007, entitled "INTESTINAL BYPASS USING MAGNETS" the entire contents of which are incorporated herein by reference.

FIELD OF THE INVENTION

This invention relates to medical devices and methods for the treatment of obesity, and more particularly to forming an intestinal bypass anastomosis using magnets.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition.

More invasive approaches have been available which have yielded good results in many patients. These include surgical options such as bariatric surgery, bypass surgery or gastroplasty. However, these procedures carry high risks, and are therefore not appropriate for many patients. Even when carried out laparoscopically, these procedures are still considered major surgery due to the high risk and complication rates.

BRIEF SUMMARY OF THE INVENTION

The present invention provides medical devices and methods for forming an intestinal bypass anastomosis for the treatment of obesity that is minimally invasive with reduced complications. According to one embodiment, a method of forming an anastomosis between a proximal section and a distal section of the digestive tract is provided in accordance with the teachings of the present invention. As one example, the anastomosis may bypass a portion of the small intestine to create a malabsorptive effect and induce weight loss. A first magnet assembly is placed within the distal section, and a second magnet assembly is placed within the proximal section of the digestive tract. An opening is formed within a wall of a bodily lumen. Medical instrumentation is passed through the opening and is used to engage the distal portion section proximate the first magnet assembly. The distal section is moved such that the first magnet assembly becomes magnetically coupled to the second magnet assembly. An anastomosis is formed proximate the first and second magnet assemblies.

According to more detailed aspects of this embodiment, the medical instrumentation is preferably capable of being steered, and may take many forms. For example, the medical instrumentation may include a steerable endoscope having a grasping device positioned within a working channel of the endoscope. Likewise, the medical instrumentation may include a directing catheter or a steerable wire guide having a magnetic tip. When the medical instrumentation includes a magnetic portion, the step of engaging the distal section includes magnetically coupling the magnetic portion with the first magnet assembly. The medical instrumentation also preferably includes fiber optic imaging capabilities, whereby the engaging step includes visualizing the distal portion of the small intestine. To assist in the location of the first magnet assembly by the medical instrumentation, a signal emitter may be placed within the distal section proximate the first magnet assembly. The medical instrumentation would include a sensor capable of detecting a signal from the signal emitter. The anastomosis forming step may include allowing the first and second magnet assemblies to engage over an area and induce necrosis of the tissue within the area, or may include introduction of an endoscopic cutting instrument proximate the magnet assemblies and excising tissue of the selected bodily lumens.

According to another embodiment constructed in accordance with the teachings of the present invention, a medical instrument is provided for engaging a first magnet assembly and magnetically coupling it to a second magnet assembly to form an anastomosis. The medical instrument generally comprises a directing catheter having a magnetic portion and a pushing catheter defining a lumen receiving the directing catheter. The second magnet assembly defines an aperture sized to receive the directing catheter, and is positionable along the outer periphery of the directing catheter. Relative translation of the pushing catheter and directing catheter causes the second magnet assembly to move distally over the directing catheter for engagement with the first magnet assembly.

According to more detailed aspects of the medical instrument, the aperture in the second magnet assembly is sized smaller than an outer diameter of the pushing catheter. The directing catheter is preferably steerable for navigation and engagement with a first magnet assembly. When the magnetic portion of the directing catheter is magnetically coupled to the first magnet assembly, withdrawal of the directing catheter substantially within the lumen of the pushing catheter causes decoupling of the magnetic portion and the first magnet assembly. The magnetic center line of the magnetic portion may be generally parallel to the magnetic center line of the magnet assembly, or alternatively may be generally perpendicular to the magnetic center line of the second magnet assembly.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
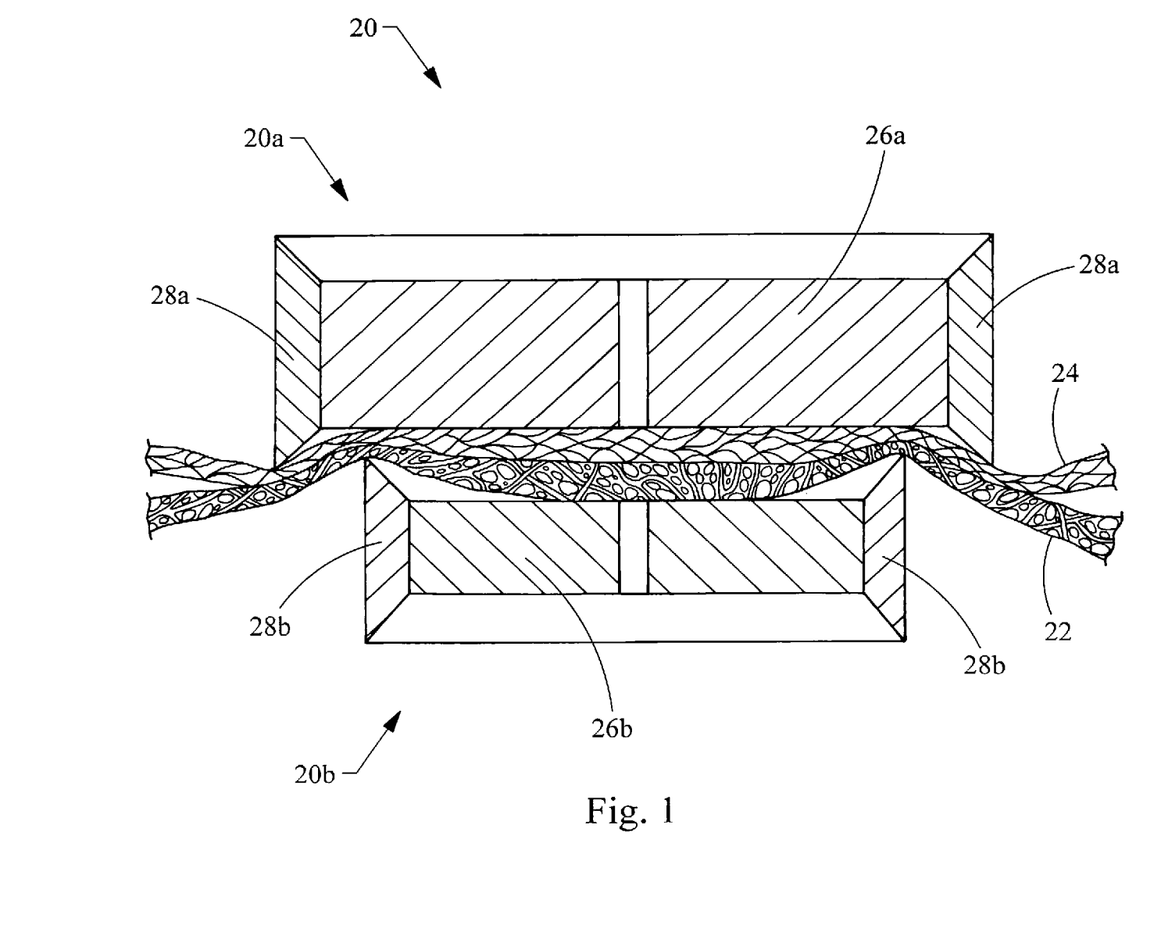
FIG. 1 is a cross-sectional view of two magnet assemblies for forming an anastomosis.

Turning now to the figures, FIG. 1 depicts a magnetic anastomosis device 20 for use in forming an intestinal bypass anastomosis to treat obesity, in accordance with the teachings of the present invention. Generally, the magnetic anastomosis device 20 includes first and second magnet assemblies 20a, 20b comprising magnetic cores 26a, 26b which are surrounded by thin metal rims 28a, 28b. Due to the magnetic attraction between the two magnetic cores 26a, 26b, the walls 22, 24 of two adjacent hollow organ may be sandwiched and compressed between the magnet assemblies 20a, 20b, resulting in ischemic necrosis of the walls 22, 24 to produce an anastomosis between the two hollow organ. Further details of the device 20 and related devices may be found in U.S. Pat. No. 5,690,656, the disclosure of which is incorporated herein by reference in its entirety. It will be understood by those skilled in the art that many magnetic anastomosis devices, now known or hereinafter developed, may be employed in conjunction with the present invention. For example, U.S. patent application Ser. No. 11/937,862 filed Nov. 9, 2007 and 60/978,754 filed Oct. 9, 2007 also disclose exemplary magnetic devices for forming anastomoses, which are incorporated herein by reference in their entirety.

A method of forming an anastomosis within the digestive tract will now be described with reference to FIGS. 2-5. Generally, the anastomosis will bypass a portion of the small intestine to create a malabsorptive effect, thereby inducing weight loss to treat obesity, although the bypass may be used for other medical purposes. As depicted, the digestive tract 30 generally includes an esophagus 32 leading to a stomach 34. The small intestine 36 are distal to the stomach 34, and generally include a proximal portion 40 (including the duodenum 38 and jejunum) and a distal portion 42 (which includes the ileum). The large intestine 44 (i.e. colon) leads from the small intestine 36 to the rectum 46.

Use of the terms "proximal" and "distal" in connection with the small intestine is not intended to limit these portions of the small intestine to the duodenum/jejunum and ileum, respectively. For example, a bypass may be performed between the duodenum and jejunum, two sections of the jejunum, two sections of the ileum, etc. Likewise, a bypass may be performed between different hollow organs of the digestive tract, such as stomach to small intestine, esophagus to stomach, stomach to large intestine, small intestine to large intestine, etc. Accordingly, it will be recognized that "proximal" and "distal" are used herein to simply refer to the relative position of two given sections of the digestive tract relative to each other (the mouth being proximal and the anus being distal).

Figure 2:
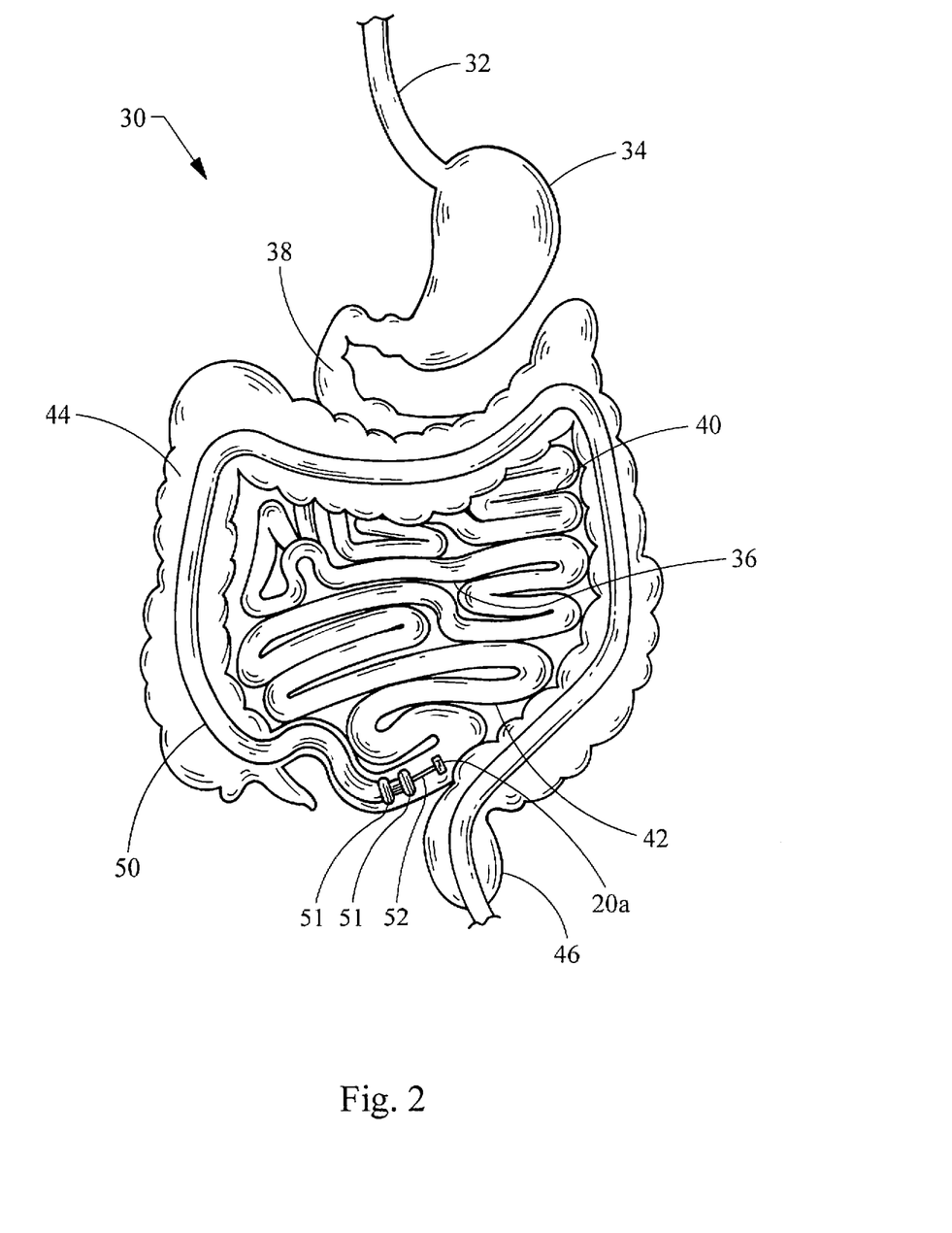
FIGS. 2-5 depict hollow organ of the digestive tract and a method of forming an anastomosis between two hollow organ of the digestive tract.

As shown in FIG. 2, the first magnet assembly 20a is placed within the distal portion 42 of the small intestine 36. This may be accomplished utilizing a standard enteroscope, and more preferably utilizing a double balloon enteroscope 50 which utilizes two inflatable balloons 51 and conventional double balloon endoscopy procedures, as is known in the art. A directing catheter 52 is utilized to position the first magnet assembly 20a beyond a distal end of the enteroscope 50 and within the distal portion 42 of the small intestine 36. It will be recognized by those skilled in the art that other minimally invasive and/or endoscopic procedures for delivering a magnet assembly within the distal portion 42 may be employed, whether now known or hereinafter developed. For example, the magnet assembly disclosed in U.S. Patent Application No. 60/978,754 may be particularly useful here, in that the magnet assembly itself is deployable between a compact configuration and a expanded deployed configuration, and only requires a small diameter catheter to deliver the magnet assembly.

Figure 3:
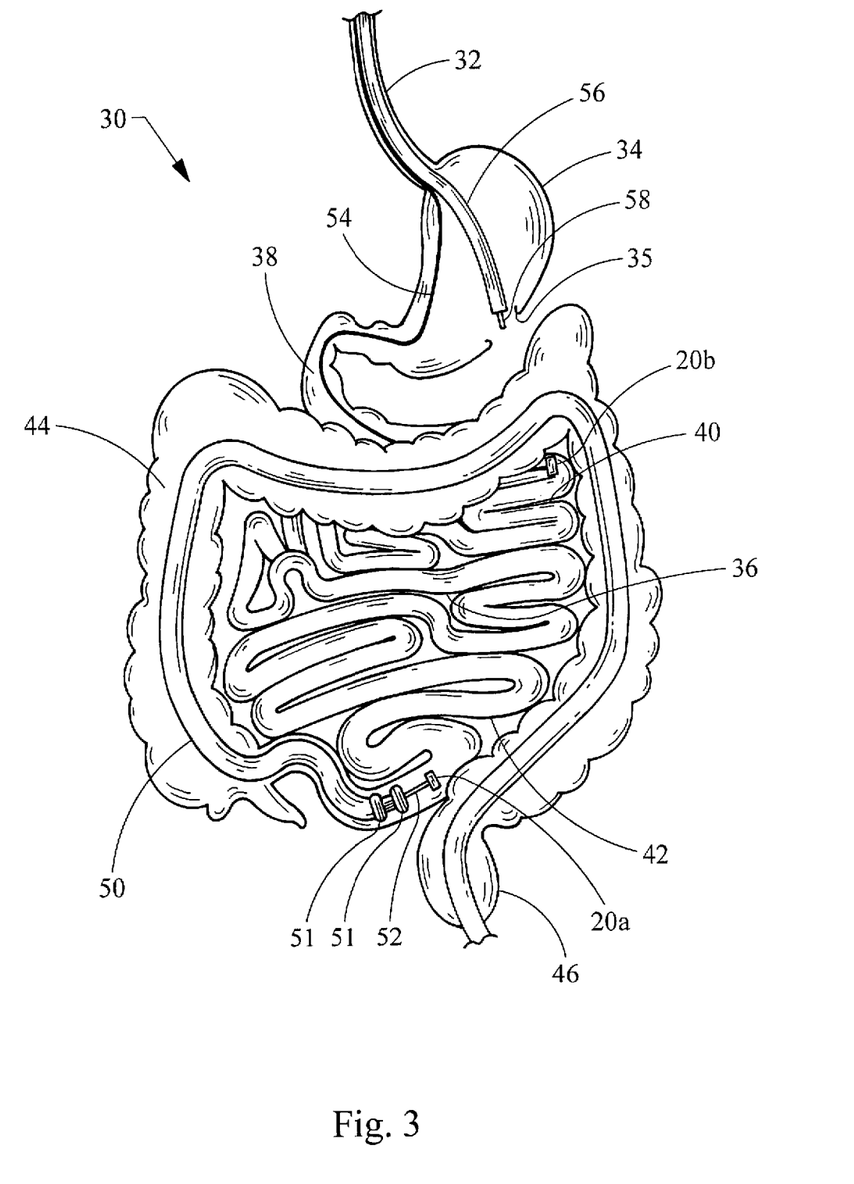

Turning now to FIG. 3, another step in the method includes placing the second magnet assembly 20b within the proximal portion 40 of the small intestine 36. A simple directing catheter 54 or the like may be utilized to deliver the second magnet assembly 20b. As will be recognized by those skilled in the art, placement of the magnet assemblies may be aided by fluoroscopy, ultrasound, fiber optic imaging or other well known guidance techniques. It will also be recognized by those skilled in the art that the second magnet assembly 20b can be placed in the stomach 34, the duodenum 38 or advanced further into the small intestine 36, as long as it is sufficiently spaced from the first magnet assembly 20a to bypass a portion of the small intestine 36.

As also shown in FIG. 3, medical instrumentation such as an endoscope 56 having a cutting element 58 is utilized to form an opening 35 in the wall of the stomach 34. The cutting element 58 is preferably an electrosurgical tool, although any cutting element capable of being endoscopically utilized may readily be employed. It will also be recognized that while access to the peritoneal cavity has been depicted via the mouth and stomach 34, access to the peritoneal cavity through any natural orifice (e.g., the mouth, anus or vagina) may be used to form the opening in the wall of a body lumen connected to the natural orifice to provide access to the peritoneal cavity and the small intestine 36. For example, the endoscope 56 or other device could be introduced through the anus into the large intestine 44, and a perforation formed in the large intestine 44 for accessing the peritoneal cavity.

Figure 4:
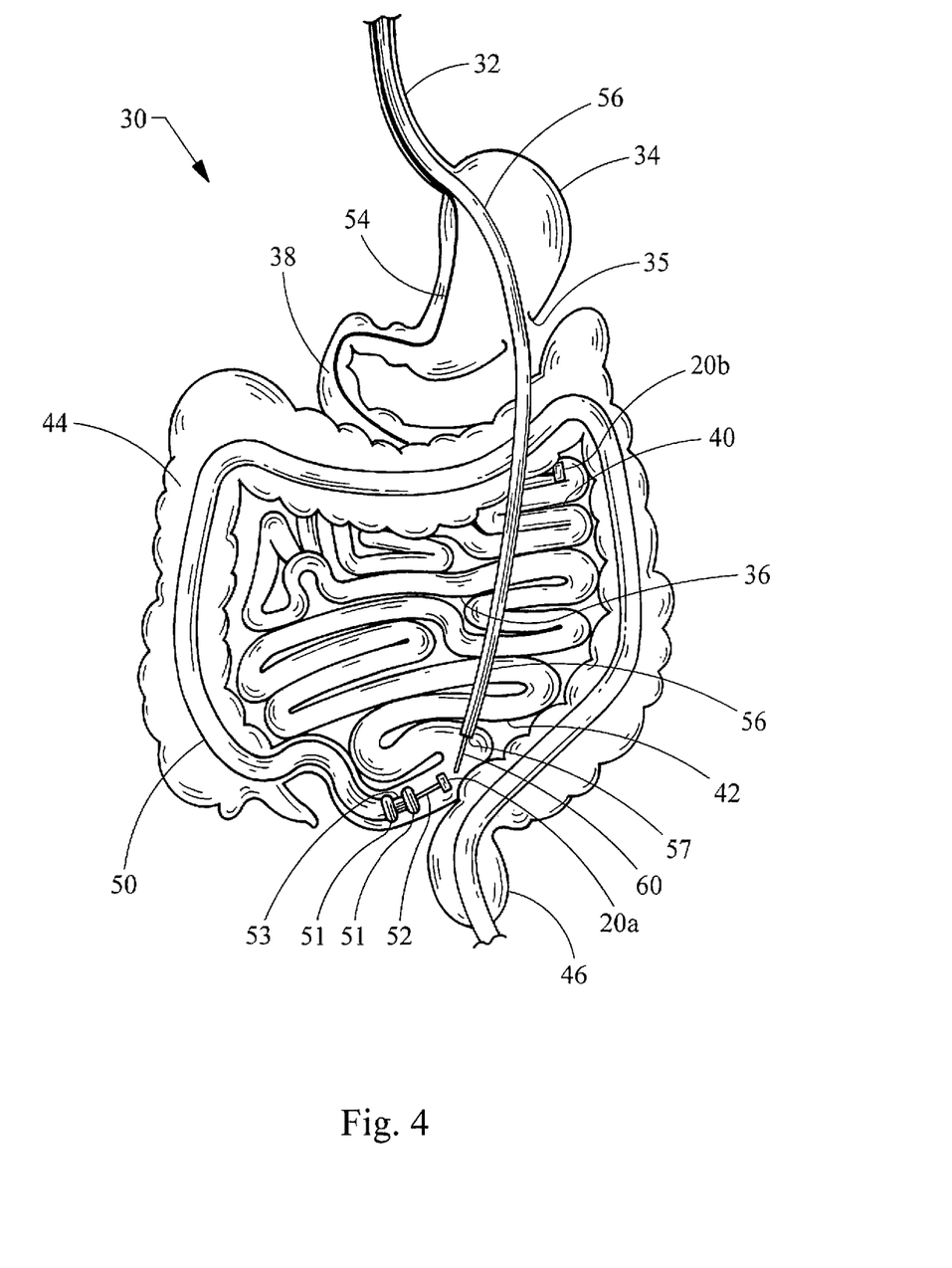

Turning to FIG. 4, the endoscope 56 is passed through the opening 35 in the stomach 34 and steered to locate the first magnet assembly 20a. Again, conventional or future developed techniques may be utilized for guiding the endoscope 56 through the peritoneal cavity to the distal portion 42 of the small intestine 36. As depicted, a grasping device 60 is advanced through a working channel of the endoscope 56, into the peritoneal cavity, and is utilized to engage the small intestine 36 proximate the first magnet assembly 20a. The location of the first magnet assembly 20a may be identified in many ways, such as using fluoroscopic, ultrasonic, fiber optics, or other imaging techniques. Preferably, the enteroscope 50 includes a signal emitter 53 at its distal end, and the endoscope 56 includes a detector 57 capable of sensing a signal from the signal emitter 53. For example, the enteroscope 50 may include a light source proximate the double balloons 51, and the fiber optic imaging capabilities of the endoscope 56 may be utilized to visualize the light source. The enteroscope 50 may also be removed and the first magnet assembly 20a may be located blindly or under fluoroscopy, etc. Again, conventional or future developed techniques may be utilized for guiding the endoscope 56 to the distal portion 42 of the small intestine 36, including imaging devices that are built into or deployed in parallel with the grasping device 60, such as catheter based imaging systems, or emitters built into the first magnet assembly 20a.

Figure 5:
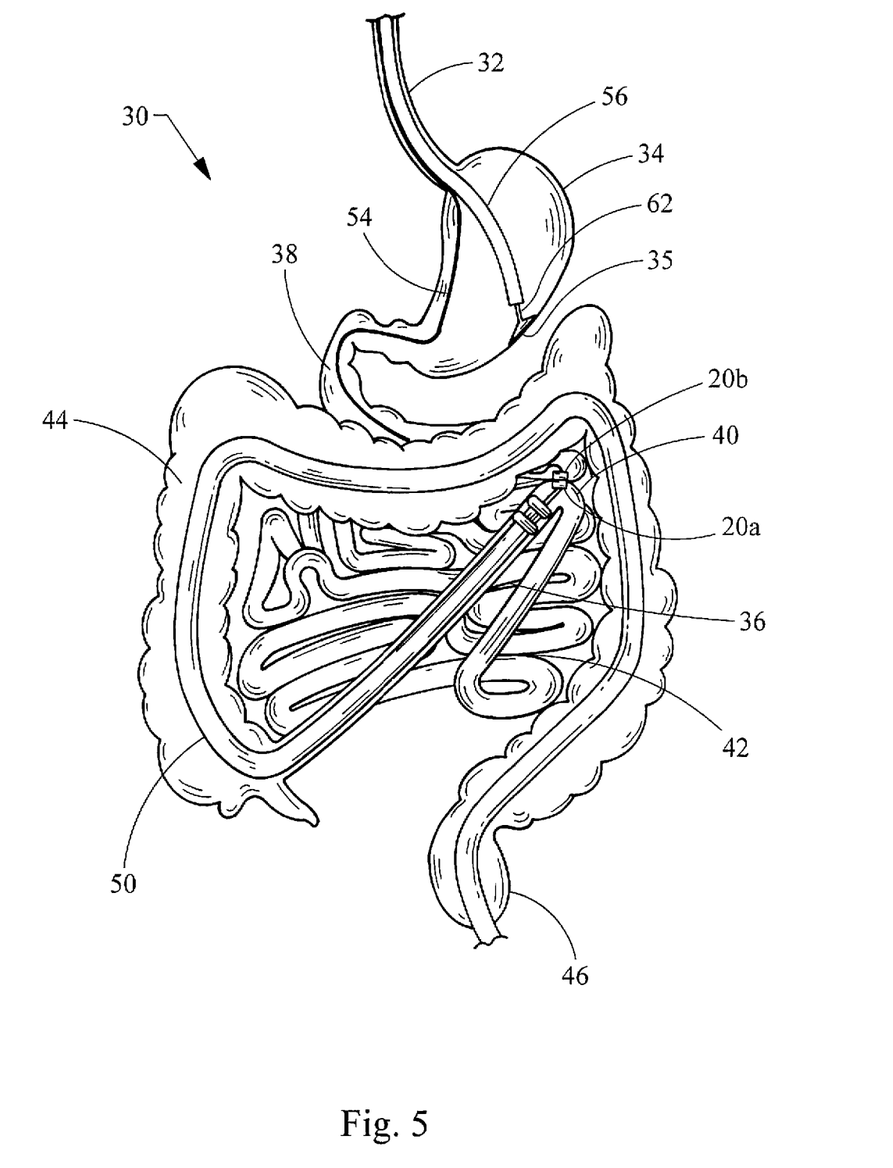

As depicted in FIG. 5, the endoscope 56 and its grasping device 60 are then utilized to bring the distal portion 40 of the small intestine 36, including the first magnet assembly 20a, into close proximity with the second magnet assembly 20b such that the two magnet assemblies are magnetically coupled. An anastomosis is then formed between the proximal portion 40 and distal portion 42 of the small intestine 36. The anastomosis may be formed by allowing the magnet assemblies 20a, 20b to engage over an area and induce necrosis of the tissue within the area to form the anastomosis, such as is described in U.S. Pat. No. 5,690,656. The first and second magnet assemblies 20a, 20b may also be used to approximate the tissue and permit excision of the tissue by a cutting device, thereby more immediately forming the anastomosis, such as is described in U.S. patent application Ser.

No. 11/937,862. It will be recognized that many methods of endoscopically forming an anastomosis utilizing magnets may be employed in conjunction with the present invention.

Also shown in FIG. 5, the opening 35 in the stomach 34 is then closed utilizing a suturing device 62 or other tissue repair tool that can be endoscopically employed. As they are no longer needed, the enteroscope 50 and endoscope 56 may be withdrawn. The bypassed portion of in the small intestine 36 (both leading to and from) may then be closed off utilizing conventional suturing techniques or other known techniques, although the bypassed portion may also be left open, depending on the particular portions of the digestive tract involved. It will be recognized that a laparoscopic approach may be used to bring the first and second magnet assemblies 20a, 20b together, rather than the method described above. For example, a grasping instrument deployed laparoscopically may be used to grasp the first magnet assembly 20a and move it into connection with the second magnet assembly 20b, preferably with an imaging device or system as described above.

Figure 6:
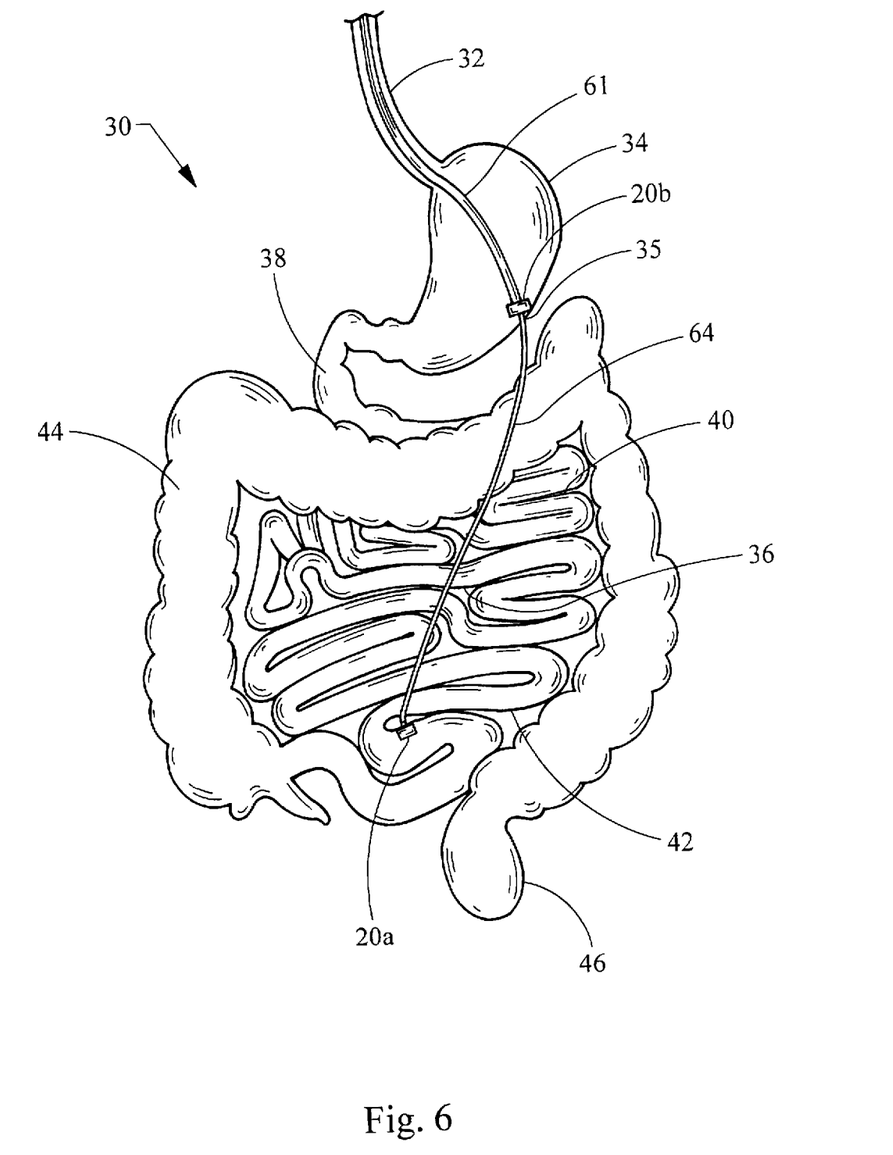
FIG. 6 depicts hollow organ of the digestive tract and another embodiment of a method for forming an anastomosis between two hollow organ of the digestive tract.

Turning now to FIG. 6, an alternative embodiment of the method of forming an anastomosis to bypass a portion of the small intestine will be described. A first magnet assembly 20a is placed in the distal portion 42 of the small intestine 36 using the steps previously described. Likewise, an opening 35 is formed within a wall of a bodily lumen, depicted here as the stomach 34. However, in this embodiment a smaller opening 35 may be formed because a smaller diameter catheter-based system is utilized. Generally, a pushing catheter 61 having a directing catheter 64 is utilized to connect the first and second magnet assemblies 20a, 20b.

Figure 7:
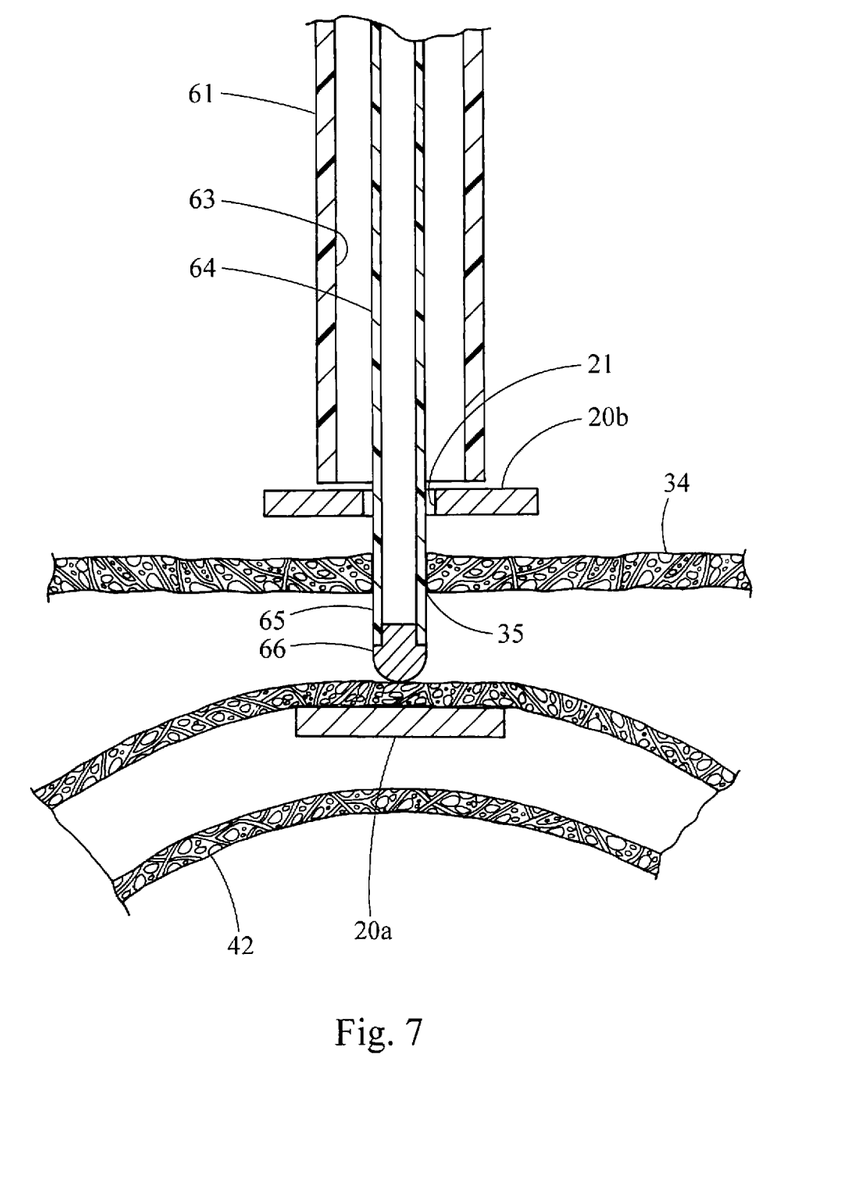
FIG. 7 is a cross-sectional view depicting a medical device used to form an anastomosis with two magnet assemblies.

As best seen in FIG. 7, the pushing catheter 61 defines a lumen 63 slidably receiving the directing catheter 64. The directing catheter 64 includes a distal end 65 having a magnetic portion 66. The magnetic portion 66 has been depicted as a simple atraumatic-shaped end cap fitted to the interior lumen of the directing catheter 64. It will be recognized by those skilled in the art that the magnetic portion 66 as well as the directing catheter 64 may take numerous forms (see, e.g., U.S. Pat. Nos. 3,358,676 and 5,383,849 the disclosures of which are hereby incorporated by reference in their entirety). Of course, the directing catheter 64 can be replaced by other elongate elements such as a steerable wire guide, one exemplary wire guide being disclosed in U.S. Pat. No. 6,805,676, the disclosure of which is hereby incorporated by reference in its entirety. The directing catheter 64 is navigated to the first magnet assembly 20a such that the magnetic portion 66 becomes magnetically coupled thereto and engaged with the distal portion 42 of the small intestine 36 (FIG. 6).

Figure 8:
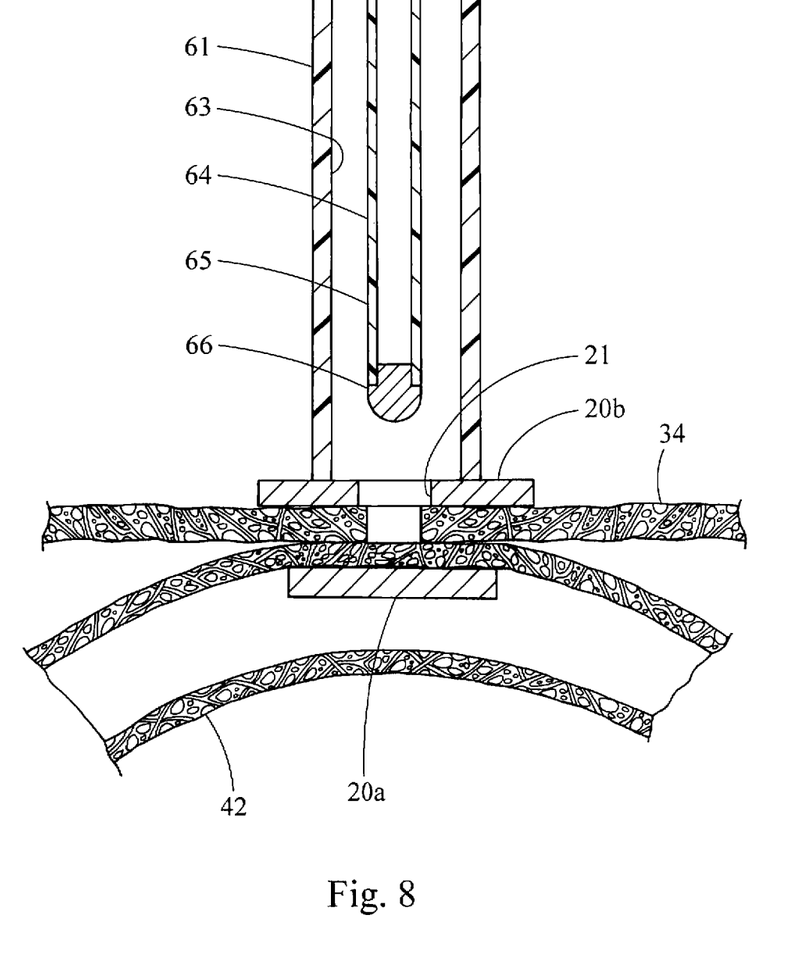
FIG. 8 is a cross-sectional view depicting the medical device of FIG. 7 in another configuration.

It can also be seen in FIG. 7 that the second magnet assembly 20b defines an aperture 21 sized to receive the directing catheter 64 therein. The aperture 21 is sized small than an outer diameter of the pushing catheter 61 such that the pushing catheter 61 may deliver the second magnet assembly 20b into engagement with the first magnet assembly 20a. The directing catheter 64 is then retracted proximally such that the first magnet assembly 20a is brought into the vicinity of the stomach 34 and the second magnetic assembly 20b, as shown in FIG. 7. As shown in FIG. 8, the directing catheter 64 is then translated relative to the pushing catheter 61 such that the magnetic portion 66 of the directing catheter 64 is withdrawn substantially inside the lumen 63 of the pushing catheter 61, thereby pushing the second magnet assembly 20b into magnetic attraction with the first magnet assembly 20a. With the first and second magnet assemblies 20a, 20b approximating the tissues of the stomach 34 and the distal portion 42 of the small intestine 36, an anastomosis may be formed using the previously described steps.

Figure 9:
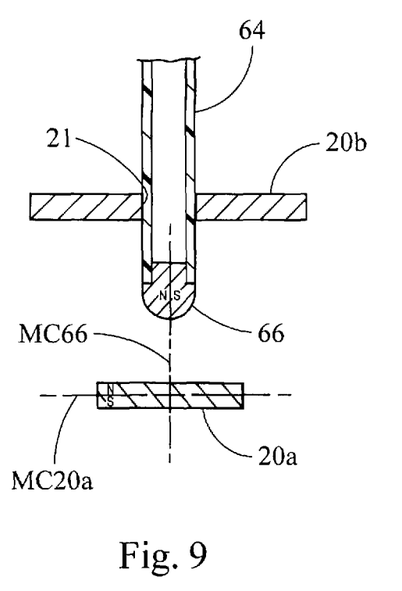
FIG. 9 is a schematic view depicting a portion of the medical device of FIG. 7.
Figure 10:
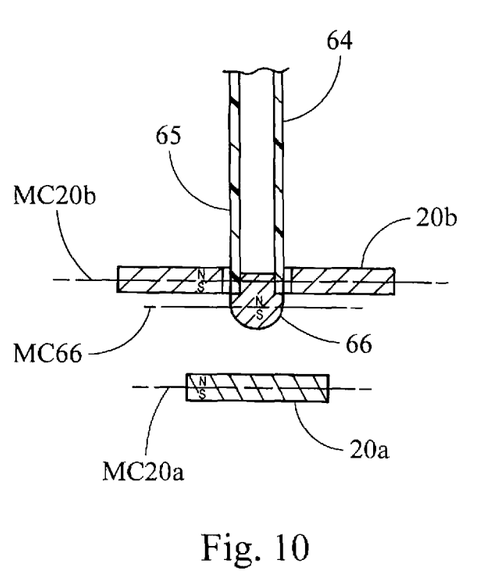
FIG. 10 is a schematic view similar to FIG. 9 depicting an alternate construction of the magnetic device of FIG. 7.

As shown in FIGS. 9 and 10, the orientation of the magnetic poles (indicated as "N" and "S") may take several forms. For example, in FIG. 9 the magnetic portion 66 of the directing catheter 64 has been shown having north (N) and south (S) poles separated by a magnetic center line MC66 that extends perpendicular to the magnetic center line MC20a of the first magnet assembly 20a. In FIG. 10, the magnetic center line MC66 of the magnetic portion 66 has been shown generally parallel to the magnetic center line MC20a of the first magnet assembly 20a, as well as parallel to the magnetic center line MC20b of the second magnet assembly 20b.

It will be recognized that the magnetic portion 66 and the directing catheter 64 are designed to retain the second magnet assembly 20b proximate the distal end 65 thereof. In the embodiment of FIG. 10, the magnetic portion 66 and second magnet assembly 20b are magnetically attracted, as shown. Relative translation of the directing catheter 64 and pushing catheter 61 will be sufficient to overcome the magnetic attraction (and repulsion) of the second magnet assembly 20b and magnetic tip 66 in order to magnetically couple the first and second magnet assemblies 20a, 20b. In the embodiment of FIG. 9, the second magnet assembly 20b has an aperture 21 that is sized to frictionally engage the exterior of directing catheter 64, but remains slidable relative thereto to permit magnetic coupling of the first and second magnet assemblies 20a, 20b through relative translation of the directing catheter 64 and pushing catheter 61.

Accordingly, it will be recognized by those skilled in the art that a minimally invasive method for bypassing a portion of the digestive tract (e.g., the small intestine) is provided to create a malabsorptive effect and induce weight loss. The complications and other problems utilizing conventional surgical or laparoscopic techniques are minimized or avoided, while retaining control over placement of the anastomosis and hence the bypassed portions of the small intestine.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of forming an anastomosis between a proximal section of the digestive tract and distal section of the digestive tract, the method comprising the steps of:
   placing a first magnet assembly within the distal section;
   placing a second magnet assembly within the proximal section;
   forming an opening within a wall of a bodily lumen adjacent the proximal section;
   passing medical instrumentation through the opening;
   engaging the distal section proximate the first magnet assembly with the medical instrumentation while the medical instrumentation is passed through the opening and without passing the medical instrumentation through a wall of the distal section;

moving the distal section with the medical instrumentation such that the first magnet assembly becomes magnetically coupled to the second magnet assembly, wherein the first and second magnet assemblies are sized and structured to engage over an area and induce necrosis of tissue within the area to form the anastomosis; and forming an anastomosis between the proximal and distal sections of the digestive tract proximate the first and second magnet assemblies.

2. The method of claim 1, wherein the medical instrumentation is capable of being steered.

3. The method of claim 2, wherein the medical instrumentation includes a steerable endoscope having a grasping device positioned within a working channel of the endoscope.

4. The method of claim 2, wherein the medical instrumentation includes a directing catheter having a magnetic tip.

5. The method of claim 2, wherein the medical instrumentation includes a steerable wire guide having a magnetic tip.

6. The method of claim 1, wherein the medical instrumentation includes a magnetic portion, and wherein the step of engaging the distal section includes magnetically coupling the magnetic portion with the first magnet assembly.

7. The method of claim 6, further comprising the step of decoupling the magnetic portion of the medical instrumentation from the first magnet assembly.

8. The method of claim 7, wherein the medical instrumentation includes an elongage member having the magnetic portion and a pushing catheter defining a lumen receiving the elongage member, and wherein the second magnet assembly includes an aperture sized to receive the elongage member, and wherein the decoupling step comprises translating the pushing catheter and elongage member relative to one another such that the elongage member is substantially withdrawn into the lumen of the pushing catheter and the pushing catheter is detached from the second magnet assembly.

9. The method of claim 8, wherein the opening in the bodily lumen is sized to receive the directing catheter therethrough and prevent passage of the second magnet assembly therethrough.

10. The method of claim 1, further comprising the step of introducing a signal emitter within the distal section proximate the first magnet assembly, and wherein the medical instrumentation includes a sensor capable of detecting a signal from the signal emitter.

11. The method of claim 1, wherein the forming step includes introducing an endoscopic cutting instrument proximate the magnetically engaged first and second magnet assemblies, and excising tissue of the proximal and distal sections proximate the first and second magnet assemblies to form the anastomosis.

12. The method of claim 1, wherein the step of placing the first magnet assembly occurs via a natural orifice.

13. The method of claim 1, wherein the step of placing the second magnet assembly occurs via a natural orifice.

14. The method of claim 1, wherein the step of passing medical instrumentation through the opening occurs while the second magnet assembly is within the proximal section.

15. The method of claim 1, wherein the step of forming an anastomosis includes leaving the first and second magnet assemblies within the proximal and distal sections for a sufficient period of time to induce necrosis of tissue.

16. The method of claim 1, wherein the step of moving the distal section with the medical instrumentation occurs after the step of engaging the distal section with the medical instrumentation.

17. The method of claim 1, further comprising the step of decoupling the magnetic portion of the medical instrumentation from the first and second magnet assemblies after the first and second magnet assemblies are magnetically coupled and leaving the first and second magnet assemblies in vivo to induce the necrosis.

18. The method of claim 1, wherein the step of passing medical instrumentation is performed while the medical instrumentation is not connected to the first magnet assembly.

19. The method of claim 1, wherein the medical instrumentation is moveable independently of movement of the second magnet assembly during the step of passing the medical instrumentation through the opening.

* * * * *